(12) United States Patent
Boehm

(10) Patent No.: US 8,088,949 B2
(45) Date of Patent: Jan. 3, 2012

(54) PROCESS FOR PURIFYING L-CYSTEINE

(75) Inventor: Andreas Boehm, Munich (DE)

(73) Assignee: Wacker Chemie AG, Munich (DE)

( * ) Notice: Subject to any disclaimer, the term of this patent is extended or adjusted under 35 U.S.C. 154(b) by 504 days.

(21) Appl. No.: 12/026,567

(22) Filed: Feb. 6, 2008

(65) Prior Publication Data

US 2008/0190854 A1    Aug. 14, 2008

(30) Foreign Application Priority Data

Feb. 14, 2007    (DE) .......................... 10 2007 007 333

(51) Int. Cl.
    *C07C 227/00*    (2006.01)
(52) U.S. Cl. .......................... 562/554; 210/661; 210/668
(58) Field of Classification Search .................. None
    See application file for complete search history.

(56) References Cited

U.S. PATENT DOCUMENTS

| | | | |
|---|---|---|---|
| 5,972,663 A | 10/1999 | Winterhalter et al. | |
| 6,218,168 B1 | 4/2001 | Leinfelder et al. | |
| 6,372,912 B1 | 4/2002 | Döring et al. | |
| 2005/0221453 A1 | 10/2005 | Takagi et al. | |

FOREIGN PATENT DOCUMENTS

| | | |
|---|---|---|
| DE | 100 40 176 A1 | 3/2002 |
| EP | 0 250 987 B1 | 12/1990 |
| EP | 0 885 962 A1 | 12/1998 |
| EP | 0 858 510 B1 | 12/2001 |
| EP | 1 059 288 B1 | 7/2002 |
| EP | 1 234 874 A1 | 8/2002 |
| EP | 1 220 940 B1 | 1/2003 |
| EP | 1298200 A2 * | 4/2003 |
| EP | 1528108 A1 | 5/2005 |
| EP | 1 571 223 A2 | 9/2005 |
| EP | 1571223 A2 | 9/2005 |
| EP | 1 298 200 B1 | 3/2006 |
| EP | 1 645 623 A1 | 4/2006 |
| EP | 1 650 296 A1 | 4/2006 |
| JP | 58216692 A | 12/1983 |
| JP | 2005137369 A | 6/2005 |
| JP | 2005245311 A | 9/2005 |
| WO | WO-01/27307 A1 | 4/2001 |

OTHER PUBLICATIONS

De Dardel et al, 2009, Ion Exchangers in Ulman's Encyclopedia of Industrial applications.*
US 5,972,663 is corresponding to EP 0 885 962 A1.
US 6,218,168 B1 is corresponding to EP 0 858 510 B1.
WO 01/27307 A1 is corresponding to EP 1 220 940 B1.
US 6,372,912 B1 is corresponding to EP 1 059 288 B1.
Patbase abstract corresponding to DE 100 40 176 A1.
Hollemann et al., Wiberg et al., Lehrbuch der anorganischen Chemie (Textbook of inorganic chemistry), 91st to 100th edition, Walter de Gruyter, 1985, pp. 485-523.
De Dardel et al., Arden et al., Ion Exchangers, Ullmann's Encyclopedia of Industrial Chemistry, vol. A14, p. 451.
Operation of ion-exchange chromatography (2); Factors regarding separability http://www.gelifesciences.co.jp/newsletter/biodirect_mail/technical_tips/tips52.asp, Sep. 2006 (Japanese).
English Translation of Operation of ion-exchange chromatography (2); Factors regarding separability http://www.gelifesciences.co.jp/newsletter/biodirect_mail/technical_tips/tips52.asp, Sep. 2006 (Japanese).

* cited by examiner

*Primary Examiner* — Sudhakar Katakam
(74) *Attorney, Agent, or Firm* — Brooks Kushman P.C.

(57) ABSTRACT

L-cysteine-is separated from an L-cysteine-containing fermenter broth containing an oxidizing agent which is capable of oxidizing L-cysteine at pH<5, by contacting the L-cysteine-containing fermenter broth with an ion exchanger at a pH from 5 to 9, the pH in the fermenter broth becoming <5, and preferably <2. The L-cysteine binds to the ion exchanger and the bound L-cysteine is then removed from the ion exchanger by means of an eluant.

7 Claims, No Drawings

PROCESS FOR PURIFYING L-CYSTEINE

BACKGROUND OF THE INVENTION

1. Field of the Invention

The invention relates to a process for purifying L-cysteine from an L-cysteine-containing fermenter broth.

2. Background Art

L-Cysteine is an amino acid which, owing to good solubility in water and high sensitivity of the SH group toward a multiplicity of reagents, for example toward oxidizing agents, can be purified and isolated only with very great difficulties and great expense. In contrast, the amino acid L-cystine can be purified and isolated readily and with very high purity, even from complex substance mixtures such as, for example, protein hydrolysates or L-cystine-containing fermenter broths, owing to very low solubility in water and comparatively high stability, for example toward oxidizing agents. DE10040176A1, for example, describes a very simple process for isolating L-cystine from cell-containing suspensions or fermenter broths.

Therefore, L-cysteine is industrially produced from complex mixtures such as, protein hydrolysates (e.g. from human hair or animal sources (e.g. feathers or bristles)) or appropriate fermenter broths by firstly isolating the sparingly soluble L-cystine in a purified form. L-Cysteine or other L-cysteine derivatives which may be present in such complex substance mixtures are specifically and as completely as possible converted to L-cystine, for example by way of oxidation. L-cystine is then reduced by way of subsequent reduction (e.g. by electrolysis) to give L-cysteine. However, this process has disadvantages, since L-cysteine must be prepared in a complicated, two-stage process via the intermediate L-cystine.

EP0250987B1 describes direct isolation of L-cysteine from a solution containing L-cysteine, L-cystine, L-serine and an inorganic salt. Firstly, L-cystine and the inorganic salt are crystallized at at least 20° C. by adding hydrogen chloride and removed by filtration. From the remaining solution which still contains L-cysteine and L-serine, L-cysteine hydrochloride monohydrate is then crystallized and isolated with high purity at no more than 10° C. However, the process is limited to solutions which contain L-cysteine, L-cystine, L-serine and an inorganic salt and does not enable L-cysteine to be obtained in high yield and purity from complex substance mixtures such as protein hydrolysates or fermentation broths.

EP1645623A1, EP1298200B1, US20050221453A1, EP1234874A1 and EP1571223A2 describe isolating L-cysteine from fermentation broths by means of a combination of ion exchange, crystallization and other known methods. However, no information on the specific procedure, or on the yields and purities obtained, is given.

EP 1650296A1 describes isolating L-cysteine from fermentation broths by removing the solids by centrifugation or membrane filtration and subsequently isolating and purifying the amino acid by means of ion exchange, concentration and crystallization. Here too, no information is given on the specific procedure, or on the yields and purities obtained.

Thus, the problem of directly and cost-effectively purifying and producing L-cysteine from complex substance mixtures such as, for example, L-cysteine-containing fermenter broths of a microorganism remains unsolved. No process has been disclosed which can be implemented on an industrial scale and by which L-cysteine can be obtained in high purity and/or yield from L-cysteine-containing fermenter broths in a cost-effective, direct manner and without derivatization, for example by means of oxidation to give L-cystine and subsequent reduction to give L-cysteine.

EP0885962B1, EP0858510B1 and EP1220940B1 describe processes for fermentative production of L-cysteine. These processes enable fermentation broths containing large amounts of L-cysteine to be accessed in a cost-effective manner.

Such an L-cysteine-containing fermenter broth is an extremely complex substance mixture. Apart from L-cysteine it usually contains L-cystine which is readily formed from L-cysteine under the fermentation conditions, in particular due to oxidation by available oxygen. Furthermore, in the presence of aldehydes or ketones, corresponding hemithioketals and/or thiazolidine derivatives of L-cysteine may be present, as described, for example, in EP0885962B1. The fermenter broths may also contain small amounts of other amino acids or derivatives thereof. They also usually contain carbohydrates, salts of organic and inorganic cations and anions, for example alkali metal salts and alkaline earth metal salts, and traces of heavy metal salts (e.g. Fe, Cu, Mn, Zn, etc.), dyes and further contaminations and additives such as, for example, undesired metabolic products of the microorganisms used in the fermentation. The fermenter broths, as described, for example, in EP0885962B1, EP0858510B1 and EP1220940B1, may further also contain the raw materials and ingredients used in the fermentation, for example customary carbon sources such as glucose, lactose, starch and the like, nitrogen sources such as ammonia/ammonium or proteins or protein hydrolysates and the like, and sulfur sources such as, for example, sulfide, sulfite, sulfate, thiosulfate or dithionite and the like. Since L-cysteine is a sulfur-containing amino acid, a sulfur source such as, for example, sulfide, sulfite, sulfate, thiosulfate or dithionite is usually fed in during the fermentation, in order to provide a sufficient amount of sulfur required for the formation of L-cysteine. The fermenter broths furthermore also contain dissolved oxygen, due to the oxygen introduced during fermentation. Said fermenter broths usually have a pH of 7, as described, for example, in EP0885962B1.

L-cysteine can be oxidized, for example to L-cystine, in a fermenter broth or another solution by any oxidizing agents capable of oxidizing SH groups. Apart from L-cystine as the primary product of the oxidation of L-cysteine, more highly oxidized compounds of L-cysteine and/or L-cystine may also be produced. The result of the presence of such oxidizing agents in L-cysteine-containing fermenter broths or L-cysteine-containing solutions is therefore an immediate reduction in the yield of L-cysteine.

Examples of oxidizing agents capable of oxidizing SH groups (and therefore also L-cysteine) at pH<5 are oxygen and sulfur-oxygen compounds. These oxidizing agents are normally present in variable amounts in L-cysteine-containing fermenter broths. Sulfur-oxygen compounds such as, for example, thiosulfate either are added directly as a sulfur source during fermentation, as described in EP0885962B1, for example, or may be produced from other added sulfur sources such as, for example, sulfide, sulfite, sulfate, thiosulfate or dithionite and the like during fermentation. Thus it is possible, for example, for sulfide or hydrogensulfide, inter alia, to be readily oxidized to thiosulfate by oxygen introduced during the fermentation. The complex chemistry of sulfur-oxygen compounds and formation thereof has also been described in detail, for example, in Hollemann-Wiberg, Lehrbuch der Anorganischen Chemie, 91st to 100th edition, Walter de Gruyter, Berlin-New York, 1985, pp. 485-523.

L-Cysteine is oxidized particularly readily by oxygen as an oxidizing agent, preferably at high pH. An L-cysteine solution can be stabilized against oxidation by oxygen by lowering the pH of the solution. For example, aqueous solutions of L-cysteine hydrochloride, preferably in hydrochloric acid, are known to be substantially more stable against oxidation by oxygen than, for example, aqueous solutions of L-cysteine with a pH of 7 or higher.

In contrast, the oxidizing power toward SH groups, and thus also toward L-cysteine, of a multiplicity of sulfur-oxygen compounds increases with decreasing pH, in some cases markedly. These oxidizing agents may be present in L-cysteine-containing fermenter broths or else L-cysteine-containing solutions purified therefrom and oxidize L-cysteine only to a very low extent, if at all, at pH values occurring during fermentation, for example, but oxidize L-cysteine in some cases very well with decreasing pH, particularly at pH<5.

Examples of sulfur-oxygen compounds capable of oxidizing SH groups and therefore also L-cysteine are sulfur dioxide or sulfur trioxide, for example. Sulfur dioxide is also released upon acidification of sulfite solutions and is then able to oxidize SH groups. Thiosulfate which is a preferred sulfur source used in the fermentation of L-cysteine and which practically does not oxidize L-cysteine at pH>5, preferably at a pH of 7, as present during fermentation, oxidizes L-cysteine at a pH of <5, with oxidizing power and rate of oxidation increasing with decreasing pH.

A number of other sulfur-oxygen compounds and their ability to oxidize SH groups, preferably in acidic medium, are also described in Hollemann-Wiberg, Lehrbuch der Anorganischen Chemie, 91st-100th edition, Walter de Gruyter, Berlin-New York, 1985, pp. 485-523.

There are furthermore a number of compounds which can catalyze oxidation of SH groups. Thus, for example, heavy metal salts are known to be able to effectively catalyze oxidation of cysteine to cystine. Heavy metal salts such as iron salts or zinc salts are also frequently essential additives in fermentations and are therefore also present in the corresponding fermentation broths, usually in small amounts.

If an L-cysteine-containing solution or fermenter broth contains an oxidizing agent capable of oxidizing L-cysteine to, for example, L-cystine at pH<5, then this results in an immediate loss of yield, if such solutions or fermenter broths are acidified to pH<5. Since the preferred final product, L-cysteine hydrochloride monohydrate, is crystallized from strongly acidic solutions, a loss of yield of up to 100% of the L-cysteine present is possible, depending on the oxidizing agent content with respect to L-cysteine.

SUMMARY OF THE INVENTION

It is an object of the present invention to provide a simple, cost-effective and industrially implementable process for preparing a solution containing purified L-cysteine from an L-cysteine-containing fermenter broth. It is then possible to obtain from these solutions, if required, L-cysteine, L-cysteine hydrochloride or L-cysteine hydrochloride monohydrate as a solid, for example by crystallization. These and other objects are achieved by a process in which an L-cysteine-containing fermenter broth comprising an oxidizing agent which is capable of oxidizing L-cysteine at pH<5 is contacted with an ion exchanger at a pH from pH 5 to 9, with the pH in the fermenter broth becoming <5, preferably <2, the L-cysteine binding to the ion exchanger, and the bound L-cysteine being removed from the ion exchanger by means of an eluant.

DETAILED DESCRIPTION OF THE PREFERRED EMBODIMENT(S)

An L-cysteine-containing fermenter broth can be obtained as described previously. This fermenter broth is purified with the aid of an ion exchanger, preferably after the cells and solids have been removed. Ion exchangers which may be used are acidic or basic ion exchangers. Since L-cysteine is an amphoteric compound, binding and purification to both an acidic and a basic ion exchanger are possible. Acidic and basic ion exchangers are known and commercially available. ULLMANN'S ENCYCLOPEDIA OF INDUSTRIAL CHEMISTRY, Vol. A14, p. 451 lists a selection of various suitable materials. They comprise, for example, carboxylic acid groups (weakly acidic ion exchangers), sulfonic acid and phosphonic acid groups (strongly acidic ion exchangers), quaternary ammonium groups (strongly basic ion exchangers) or amine groups (weakly basic ion exchangers) as active ion-exchanging groups. Cations or anions may be bound as counterions of the active ion-exchanging groups to the ion exchanger. Acidic ion exchangers are frequently used in the protonated H+ form, but ammonium ions, alkali metal and/or alkaline earth metal ions, for example, are also further common counterions. Basic, in particular strongly basic ion exchangers, are frequently used in the OH— form but chloride and other anions described in the prior art, for example, are also further common counterions.

Preference is given to using acidic and strongly acidic ion exchangers, and particular preference is given to using strongly acidic ion exchangers. For this purpose, the L-cysteine-containing fermenter broth is contacted with a strongly acidic cation exchanger. This may be carried out, for example, by pumping the fermenter broth over a column packed with a strongly acidic cation exchanger. The cation exchanger is preferably used in the $H^+$ form. However, it is also possible in principle to use ion exchangers with other counterions.

The pH of the applied fermenter broth is pH 5-9 and preferably pH 5-7, since otherwise, depending on the amount of the oxidizing agent, the yield may be markedly reduced due to oxidation of L-cysteine.

In comparison, an L-cysteine-containing solution or fermenter broth which contains only very small amounts of, or no, corresponding oxidizing agent can in principle be applied at any pH of 1-14. If a strongly acidic cation exchanger is used, the solution may then be preferably treated at pH 1-5, since L-cysteine binds to the ion exchanger particularly effectively at these pH values and, in the absence of an interfering oxidizing agent, no oxidation and thus also no loss of L-cysteine occurs.

If an L-cysteine-containing solution or fermenter broth is contacted with a cation exchanger, preferably a strongly acidic cation exchanger in the $H^+$ form, L-cysteine is bound virtually quantitatively to the cation exchanger during this process. Other amino acids, for example L-cystine, and/or other cations which may be present in the fermenter broth may also bind to the resin. A suitable choice of adsorption conditions (flow rate, loading, concentration, temperature, resin, etc.), however, can in some cases markedly minimize binding of these contaminants. A multiplicity of other contaminants such as neutral compounds, anions, or their corresponding acids, do not bind to the resin and are present in the eluate. In addition, anionic oxidizing agents, their corresponding acids, and also the degradation products of these oxidizing agents do not bind to the cation exchanger. This process step therefore can achieve effective removal of these contaminants.

If the strongly acidic cation exchanger is used in the $H^1$ form, the ion exchange process results in a strong pH shift of the solution flowing through the resin directly during contact with the resin. Therefore, the pH of the L-cysteine-containing solution or fermenter broth involved in the exchange process and of the eluate leaving the cation exchanger is usually at pH<2 and frequently even at pH<1 (see examples).

The L-cysteine bound to an acidic or basic ion exchanger is then eluted from the resin with common acids, bases, or salt solutions. Acids used are preferably strong acids and most preferably hydrochloric acid. Bases used are preferably amines, and most preferably, ammonia. Particularly suitable is aqueous hydrochloric acid, an aqueous salt solution, an amine, a base, or a strong base.

When eluting with ammonia, aqueous ammonia of different normalities, preferably 0.1-12N ammonia and more preferably 1-2N ammonia, is pumped through the L-cysteine-loaded ion exchanger. The ammoniacal purified solution of L-cysteine obtained may then, for example, optionally be decolorized with activated carbon and concentrated. L-Cysteine may then, for example, be crystallized with high purity and yield or precipitated with a suitable precipitant from the concentrated solutions.

When eluting with hydrochloric acid, aqueous hydrochloric acid of different normalities, preferably 0.1-12N HCl and more preferably 1-2N HCl, is pumped through the L-cysteine-loaded ion exchanger.

The L-cysteine-containing acidic eluate no longer contains any oxidizing agent capable of oxidizing L-cysteine at pH<5. Therefore, as described in the prior art, these solutions are also stable against oxidation of L-cysteine, for example by oxygen. The oxidizing agent capable of oxidizing L-cysteine at pH<5 is either removed or eliminated during adsorption of L-cysteine to the ion exchanger or removed or eliminated in a different manner during elution of L-cysteine with acid.

Elution of L-cysteine with hydrochloric acid produces a purified HCl solution of L-cysteine. This solution may optionally be concentrated and decolorized, for example with activated carbon. The industrially and particularly important product L-cysteine hydrochloride monohydrate is crystallized after addition of HCl, where appropriate.

L-Cysteine can be obtained with a significantly higher purity than from the originally applied fermenter broth by fractionating the eluate and/or applying a gradient. A suitable choice of elution conditions, for example, enables L-cysteine (preferred elution with 1N HCl) and L-cystine (preferred elution with 2N HCl) to be separated from one another on the column (see also examples 7 and 9). This procedure is particularly advantageous because L-cystine can be removed from L-cysteine hydrochloride monohydrate only with very great difficulty by other methods, for example, during crystallization of L-cysteine hydrochloride monohydrate.

Surprisingly, L-cysteine has now been shown to be able to be adsorbed from a solution containing an oxidizing agent capable of oxidizing L-cysteine at pH<5 to an ion exchanger, preferably a cation exchanger, more preferably a strongly acidic cation exchanger in the $H^+$ form, and eluted again therefrom without significant oxidation, even if the L-cysteine-containing fermenter broth has pH values of pH<5, preferably pH<2, in these process steps.

This is particularly surprising, since distinct oxidation of L-cysteine to L-cystine is observed when an L-cysteine-containing fermenter broth comprising an oxidizing agent capable of oxidizing L-cysteine at pH<5 is acidified with common acids such as, for example, hydrochloric acid or sulfuric acid, to pH<5, preferably pH<2, as expected, the oxidation being associated with an immediate loss of yield (see examples 3 and 5). This has a decisive adverse effect on the economic viability of the process.

The L-cysteine-containing solution obtained by the process of the invention may be concentrated by distillation or decolorized by means of activated carbon. It is also possible to crystallize L-cysteine or L-cysteine hydrochloride monohydrate from these solutions and thereby achieve additional purification.

Preference is given to crystallizing L-cysteine hydrochloride monohydrate from the solution of L-cysteine obtained according to the invention. This involves concentrating the solution obtained. L-cysteine hydrochloride monohydrate is preferably crystallized from these concentrated solutions, optionally after addition of hydrochloric acid, and when appropriate, after cooling to −20° C. If the L-cysteine solution also contains, apart from L-cysteine, metal salts and/or ammonium salts or, for example, L-cystine, then it is possible to remove these compounds, for example, by fractionated crystallization. This may be carried out, for example, following the process described in EP 0250987B1, by adding hydrochloric acid at at least 20° C., and crystallizing the corresponding metal chlorides and/or ammonium chlorides and L-cystine, removing the crystallized compounds by filtration, and then crystallizing L-cysteine hydrochloride monohydrate from the HCl solutions of L-cysteine obtained, by cooling down to −20° C. and isolating and drying the L-cysteine hydrocholoride monohydrate product.

The process described enables L-cysteine to be purified effectively and with good yields in an economic fashion from an L-cysteine-containing fermenter broth. If required or desired, derivatives of L-cysteine which may be present, for example L-cystine or thiazolidine derivatives, may also be converted to L-cysteine under certain process conditions, thereby increasing the yield achieved. Thus, for example, cleavage of thiazolidine derivatives of cysteine on strongly acidic cation exchangers has been disclosed and described in EP1059288B1. Cleavage of L-cystine to give L-cysteine by adding suitable reducing agents is likewise conceivable.

The process described enables the foreign amino acid content to be reduced to <5%, preferably <1%, based on L-cysteine. It is furthermore also possible to reduce the salt content to <10%, preferably <1%, based on L-cysteine. Moreover, the process described enables L-cysteine or L-cysteine hydrochloride or L-cysteine hydrochloride monohydrate to be prepared from L-cysteine-containing fermenter broths in a purity of >98% and an optical purity of >99%.

Preference is given to microorganism cells and/or insoluble components being removed from the L-cysteine-containing fermenter broth in a first process step, before the process of the invention is carried out. This involves, for example, centrifugation, filtration, decanting, membrane filtration or any other method suitable for removing cells/solids from a fermenter broth. Such removal involves, where appropriate, the addition of an auxiliary filter means such as Celite®, activated carbon, or diatomaceous earth. This process step advantageously comprises also removing from the fermenter broth, in addition to the cells, other insoluble components, for example, cystine precipitated out of the solution or precipitates of other sparingly soluble components which may be produced during fermentation of the microorganism. Furthermore it is also possible, for example, for macromolecules such as proteins to be removed or to be adsorbed with an optionally used auxiliary filter means or activated carbon or the like, and thereby removed in this process step. The L-cysteine-containing solution obtained by means of this pretreatment also falls under the term fermenter broth in accordance with the present invention.

The following examples serve to further illustrate the invention.

Example 1

Stability of an $O_2$-Containing Solution of L-Cysteine (pH 1)

100 ml of a solution of L-cysteine (c=18 g/l) in oxygen-containing water are acidified to pH=1 with drops of 20% HCl. After 5 minutes of stirring at room temperature ("RT"), the solution has an L-cysteine content of 18 g/l and a content of <0.1 g/l of dissolved L-cystine. The solution is stable with respect to the L-cysteine content for more than 24 h.

Example 2

Stability of an $O_2$-Containing Acidic Solution of L-Cysteine (pH 5)

100 ml of a solution of L-cysteine (c=18 g/l) in oxygen-containing water are acidified to pH=5 with drops of 20% HCl. After 5 minutes of stirring at RT, the solution has an L-cysteine content of 18 g/l and a content of <0.1 g/l of dissolved L-cystine. After 24 h of stirring at RT, the solution has an L-cysteine content of 17.6 g/l and an L-cystine content of 0.4 g/l.

Example 3

Stability of a Thiosulfate-Containing Acidic Solution of L-Cysteine (pH 1)

100 ml of a solution of L-cysteine (c=18 g/l) and ammonium thiosulfate (c=2.5 g/l thiosulfate) in water are acidified to pH=1 with drops of 20% HCl. After 5 minutes of stirring at RT, the clouded solution has an L-cysteine content of 12 g/l, a thiosulfate content of <0.2 g/l and a content of 6 g/l of dissolved L-cystine. After 24 h of stirring at RT, the L-cysteine content has decreased to <5 g/l.

Example 4

Stability of a Thiosulfate-Containing Acidic Solution of L-Cysteine (pH 5)

100 ml of a solution of L-cysteine (c=18 g/l) and ammonium thiosulfate (c=2.5 g/l thiosulfate) in water are acidified to pH=5 with drops of 20% HCl. After 5 minutes of stirring at RT, the solution has an L-cysteine content of 17.5 g/l, a thiosulfate content of 2.4 g/l and a content of <0.5 g/l of dissolved L-cystine. After 24 h of stirring at RT, the L-cysteine content has decreased to 16.0 g/l.

Example 5

Stability of a Thiosulfate-Containing Acidic Fermenter Broth of L-Cysteine (pH 1)

100 ml of a fermenter broth containing microorganisms and having a pH of 7, an L-cysteine content of 18 g/l, a thiosulfate content of 2.5 g/l and a content of 1.1 g/l of dissolved L-cystine are acidified to pH 1 with drops of 20% hydrochloric acid and centrifuged for 20 minutes (8000 rpm/min) to remove the biomass and solids. The resulting clear solution has an L-cysteine content of 12 g/l, a thiosulfate content of <0.2 g/l and a content of 7 g/l of dissolved L-cystine.

Example 6

Stability of a Thiosulfate-Containing Acidic Fermenter Broth of L-Cysteine (pH 5)

100 ml of a fermenter broth containing microorganisms and having a pH of 7, an L-cysteine content of 18 g/l, a thiosulfate content of 2.5 g/l and a content of 1.1 g/l of dissolved L-cystine are acidified to pH 5 with drops of 20% hydrochloric acid and centrifuged for 20 minutes (8000 rpm/min) to remove the biomass and solids. The resulting clear solution has an L-cysteine content of 17.3 g/l, a thiosulfate content of <2.3 g/l and a content of 1.1 g/l of dissolved L-cystine.

Example 7

Purification of a Thiosufate-Containing Fermenter Broth by Means of the Process of the Invention 1000 ml of a fermenter broth containing microorganisms and having a pH of 7, an L-cysteine content of 18 g/l, a thiosulfate content of 2.5 g/l and a content of 1.1 g/l of dissolved L-cystine are acidified to pH 5 with drops of 20% hydrochloric acid, and centrifuged for 20 minutes (8000 rpm/min) to remove the biomass and solids. The resulting clear solution is pumped over a cation exchange column (200 ml of Amberlite IR 120H, strongly acidic, H+ form). In the process, L-cysteine and L-cystine are bound to the resin virtually quantitatively and substituted for protons. Where appropriate, further amino acids and also cations present in the solution are also bound to the resin. During this substitution process, the solution flowing through the resin undergoes a massive pH shift to low pH. The pH of the eluate is in the range of pH=0-1. The eluate furthermore contains a number of contaminants which do not bind to the resin (e.g. neutral compounds, anions and their corresponding acids, etc.), but only small amounts of amino acids, if any. Thiosulfate is decomposed completely due to the strongly acidic medium and can no longer be detected in the eluate. Owing to decomposition of thiosulfate in the acidic medium, the clouded eluate may contain, inter alia, colloidal sulfur.

The ion exchange column is washed with 400 ml of water and L-cysteine bound to the resin is then eluted with 1000 ml of 1N HCl. The product fractions contain more than 90% of the L-cysteine present in the applied fermenter broth and only very small amounts of L-cystine (0.3 g; <2%, based on L-cysteine). Bound L-cystine remaining on the ion exchange column (<2 g) can be eluted with 2N HCl.

Example 8

Comparative Example: Purification of a Thiosulfate-Containing Fermenter Broth/Adsorption at pH=1

1000 ml of a fermenter broth containing microorganisms and having a pH of 7, an L-cysteine content of 18 g/l, a thiosulfate content of 2.5 g/l and a content of 1.1 g/l of dissolved L-cystine are acidified to pH 1 with drops of 20% hydrochloric acid and centrifuged for 20 minutes (8000 rpm/min) to remove the biomass and solids. The resulting solution is pumped over a cation exchange column (200 ml of Amberlite IR 120H, strongly acidic, H+ form). In the process, L-cysteine and L-cystine are bound to the resin virtually quantitatively and substituted for protons. Further amino acids and also cations present in the solution may also be bound to the resin. During this substitution process, the solution flowing through the resin undergoes a further pH shift to low pH. The pH of the eluate is in the range of pH=0-1. The eluate furthermore contains a number of contaminants which do not bind to the resin (e.g. neutral compounds, anions and their corresponding acids, etc.), but only small amounts of amino acids, if any. Thiosulfate can no longer be detected in the eluate. Owing to decomposition of thiosulfate in the acidic medium, the clouded eluate may contain colloidal sulfur.

The ion exchange column is washed with 400 ml of water and L-cysteine bound to the resin is then eluted with 1000 ml of 1N HCl. The product fractions contain less than 60% of the L-cysteine present in the fermenter broth.

Example 9

Comparative Example: Purification of a Fermenter Broth Low in/Free of Thiosulfate 1000 ml of a fermenter broth containing microorganisms and having a pH of 7, an L-cysteine content of 18 g/l, a thiosulfate content of <0.1 g/l, preferably 0 g/l, and a content of 1.1 g/l of dissolved L-cystine are acidified to pH 1-5, preferably pH=3, with drops of 20% hydrochloric acid, and centrifuged for 20 minutes (8000 rpm/min) to remove the biomass and solids. The resulting clear solution (cysteine content: 17.8 g/l) is pumped over a cation exchange column (200 ml of Amberlite IR 120H, strongly acidic, H+ form). In the process, L-cysteine, L-cystine, where appropriate further amino acids and cations present in the solution, are bound to the resin virtually quantitatively and substituted for protons. During this substitution process, the solution flowing through the resin undergoes a massive pH shift to low pH. The pH of the eluate is in the range of pH=0-1. The eluate furthermore contains a number of contaminants which do not bind to the resin (e.g. neutral compounds, anions and their corresponding acids, etc.), but only small amounts of amino acids, if any. Owing to the fact that thiosulfate is present in very low amounts or not at all in the fermenter broth used (<0.1 g/l), the clear eluate does not contain any colloidal sulfur.

The ion exchange column is washed with 400 ml of water and L-cysteine bound to the resin is then eluted with 1000 ml of 1N HCl. Alternatively, L-cysteine may also be eluted with aqueous ammonia. The product fractions contain more than 90% of the L-cysteine present in the applied fermenter broth and only very low amounts of L-cystine (0.3 g; <2%, based on L-cysteine). Bound L-cystine remaining on the ion exchange column (<2 g/l) may be eluted with 2N HCl.

Example 10

Purification of the HCl Eluates of Examples 7 and 9 to Give L-Cysteine Hydrochloride Monohydrate 500 ml of a purified L-cysteine-containing solution (eluate with 1N HCl) of example 7 or 9 (L-cysteine content=17 g/l) are concentrated to 25 ml. After adding concentrated HCl or introducing HCl gas, chlorides of inorganic alkali metal and alkaline earth metal ions and ammonium chloride may be crystallized, preferably at 20-60° C. After filtration, the L-cysteine-containing mother liquor is cooled to −10° C. and L-cysteine hydrochloride monohydrate crystallizes. Depending on the purity of the L-cysteine-containing solution used, L-cysteine hydrochloride monohydrate may be obtained in crystalline form in yields of >80% and purities of >90% from these solutions. It is possible to achieve purities of up to >98% by suitable control of the crystallization conditions, fractionated crystallization and/or recrystallization.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for purifying an L-cysteine-containing fermenter broth comprising a thiosulfate oxidizing agent capable of oxidizing L-cysteine at pH<5, comprising contacting the L-cysteine-containing fermenter broth having a pH of 5 to 9 with an acidic or strongly acidic ion exchanger such that the pH in the fermenter broth becomes pH<5, the L-cysteine binding to the ion exchanger, and the bound L-cysteine is then removed from the ion exchanger by means of an eluant.

2. The process of claim 1, wherein the pH of the fermenter broth becomes <2.

3. The process of claim 1, wherein the ion exchanger used is strongly acidic ion exchanger.

4. The process of claim 3, wherein the ion exchanger used is a strongly acidic ion exchanger in the H$^+$ form.

5. The process of claim 4, wherein the eluant comprises aqueous hydrochloric acid, an aqueous salt solution, an amine, or a base.

6. The process of claim 1, wherein a first eluant is 1N HCl, eluting L-cysteine, and then a second eluant of 2N HCl is used, eluting L-cystine.

7. The process of claim 1, wherein an eluant solution obtained is concentrated, and L-cysteine hydrochloride monohydrate is then crystallized from the concentrated solution.

* * * * *